United States Patent
Waller et al.

(10) Patent No.: US 9,757,307 B2
(45) Date of Patent: Sep. 12, 2017

(54) MEDICATION ACCESS DEVICE FOR PREVENTION OF MEDICATION RESERVOIR CONTAMINATION

(75) Inventors: Stephen Waller, Overland Park, KS (US); Sara Ellen Wilson, Lawrence, KS (US); Katrina Lynn McDaniel, Glen Cove, NY (US); Lisa Ann Clough, Fairway, KS (US); Joseph Soltys, Overland Park, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 635 days.

(21) Appl. No.: 13/881,688

(22) PCT Filed: Oct. 25, 2011

(86) PCT No.: PCT/US2011/057768
§ 371 (c)(1),
(2), (4) Date: Apr. 25, 2013

(87) PCT Pub. No.: WO2012/058247
PCT Pub. Date: May 3, 2012

(65) Prior Publication Data
US 2013/0218121 A1     Aug. 22, 2013

Related U.S. Application Data

(60) Provisional application No. 61/406,343, filed on Oct. 25, 2010.

(51) Int. Cl.
A61B 19/00     (2006.01)
A61J 1/20     (2006.01)
(Continued)

(52) U.S. Cl.
CPC .............. *A61J 1/2096* (2013.01); *A61M 5/50* (2013.01); *A61M 5/5086* (2013.01);
(Continued)

(58) Field of Classification Search
CPC ........ A61J 1/2096; A61J 1/2037; A61M 5/50; A61M 5/5013; A61M 5/5066;
(Continued)

(56) References Cited

U.S. PATENT DOCUMENTS

2004/0171302 A1* 9/2004 Matkovich ......... A61M 39/1011
439/587
2006/0030832 A1  2/2006 Niedospial, Jr. et al.
(Continued)

FOREIGN PATENT DOCUMENTS

EP     0344956     12/1989
EP     2008684     12/2008
(Continued)

OTHER PUBLICATIONS

Supplementary European Search Report for EP 11836971, mailed Jan. 27, 2015.
(Continued)

*Primary Examiner* — Tatyana Zalukaeva
*Assistant Examiner* — Ariana Zimbouski
(74) *Attorney, Agent, or Firm* — Ray Quinney & Nebeker P.C.; Paul N. Taylor

(57) ABSTRACT

A safety-engineered, one-time use, syringe adaptor-connector system restricts access to medical vials and intravenous bags (e.g., common reservoirs) using a valve and providing a barrier to inserting a needle in the reservoir.

16 Claims, 14 Drawing Sheets

Figure 1A:
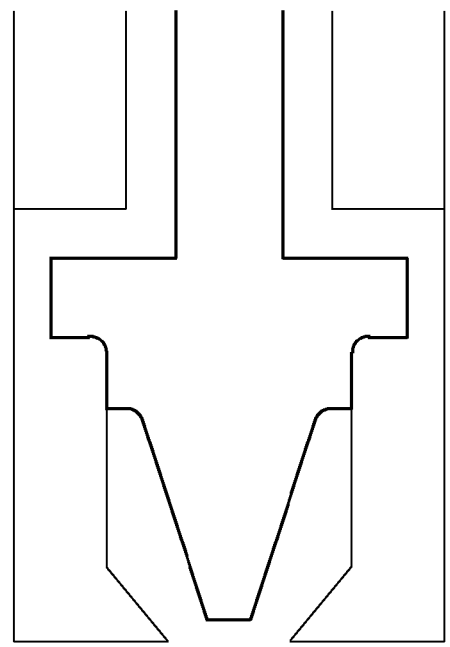

(51) Int. Cl.
*A61M 5/50* (2006.01)
*A61M 39/10* (2006.01)
*A61M 39/24* (2006.01)
*A61M 39/26* (2006.01)
*A61J 1/10* (2006.01)
*A61J 1/14* (2006.01)
*A61M 39/20* (2006.01)

(52) U.S. Cl.
CPC ............ *A61M 39/10* (2013.01); *A61M 39/24* (2013.01); *A61M 39/26* (2013.01); *A61J 1/10* (2013.01); *A61J 1/1475* (2013.01); *A61J 1/2037* (2015.05); *A61M 39/20* (2013.01); *A61M 2039/1077* (2013.01)

(58) Field of Classification Search
CPC .... A61M 5/5086; A61M 39/10; A61M 39/24; A61M 39/36; A61M 2005/5006
See application file for complete search history.

(56) References Cited

U.S. PATENT DOCUMENTS

| | | | |
|---|---|---|---|
| 2006/0089594 A1 | 4/2006 | Landau | |
| 2007/0032775 A1* | 2/2007 | Niedospial, Jr. | A61J 1/2096 604/415 |
| 2007/0293826 A1* | 12/2007 | Wall | A61M 5/19 604/200 |
| 2008/0214990 A1* | 9/2008 | Smutney | A61M 3/0279 604/27 |
| 2009/0036764 A1* | 2/2009 | Rivas | A61B 5/14 600/365 |
| 2011/0046569 A1* | 2/2011 | Lum | A61M 5/31511 604/219 |

FOREIGN PATENT DOCUMENTS

| | | |
|---|---|---|
| JP | H07213607 | 8/1995 |
| JP | H11188094 | 7/1999 |
| JP | 2005-027883 | 2/2005 |
| JP | 2005-296135 | 10/2005 |
| JP | 2007-039121 | 2/2007 |
| JP | 2008-259817 | 10/2008 |
| KR | 10-2010-0016526 | 10/2010 |
| WO | WO 200599791 | 10/2005 |
| WO | WO 2012058247 | 5/2012 |

OTHER PUBLICATIONS

PCT/US2011/057768, May 11, 2012, International Search Report.
Thompson, N.D., et al; Nonhospital Health Care—Associated Hepatitis B and C Virus Transmission: United States, 1998-2008; Ann Intern Med 2009; 150(1):33-39.

* cited by examiner

Closed

One Way
Air Valve

Open

Closed

Open

MEDICATION ACCESS DEVICE FOR PREVENTION OF MEDICATION RESERVOIR CONTAMINATION

CROSS-REFERENCE TO RELATED APPLICATIONS

This application is a U.S. Nationalization of International Application Number PCT/US2011/057768, filed on Oct. 25, 2011, which claims the benefit of and priority to U.S. Provisional Application No. 61/406,343, filed Oct. 25, 2010, which is incorporated herein by reference in its entirety.

BACKGROUND

Transmission of blood-borne infections (e.g. Hep B, Hep C, & HIV) from health care exposures was previously believed to be uncommon. However, multiple outbreaks across the United States over the last several years have shed light on this problem. In a recent article (Thompson N. D., et al., Nonhospital Health Care-Associated Hepatitis B and C Virus Transmission: United States, 1998-2008, Ann Intern Med 2009; 150(1):33-39, which is incorporated herein by specific reference in its entirety) reviewing outbreaks of nonhospital health care-associated Hep B & Hep C virus transmission in the United States from 1998-2008. 33 known outbreaks were identified. These events have resulted in 448 cases of Hep B and Hep C and >60,000 individuals exposed to potential blood-borne pathogens. As recently as October 2009, Broward General Medical Center (Florida) sent letters to >1800 patients who were potentially exposed to contaminated fluids. In this instance, the nurse routinely used the same bag of saline on multiple patients.

One such large outbreak occurred in an outpatient oncology clinic in Nebraska from 2000-2001. In this instance, the nurse would reuse a syringe to perform a saline flush. Saline for multiple patients was acquired from a common bag. More than 600 patients were notified. 99 patients were diagnosed with Hep C. These were all breaches of standard practice and should have never occurred. In many instances, veteran health care personnel were responsible for such poor practices. These cases all have in common acquisition of saline or a drug from a common container via a contaminated needle and/or syringe. Despite the increasing use of single-dose vials, such outbreaks occur as providers still use these single-dose vials on multiple individuals to contain costs.

DESCRIPTION

Presently, syringes tipped with needles or "needleless syringes" allow withdrawal of a liquid composition (e.g., saline or medication) from a reservoir. Use of a needleless device reduces the chance of an accidental stick by the operator. However, neither one of these systems prevents re-use of a contaminated syringe, needle or needleless device when acquiring more medication from the same or different reservoir. In addition, when a reservoir is accessed by a needle or a needleless device, the liquid composition is allowed to flow freely. Essentially, not only can sterile liquid flow from the reservoir to the syringe, but the contaminated syringe, needle or needleless device can contaminate the fluid, and the contaminated fluid can move up the line and contaminate the reservoir and its liquid contents. Most of the outbreaks related to liquid reservoir contamination have occurred in the outpatient setting (e.g. clinics, surgery centers, hemodialysis units). As such, the present system and methods of use can be utilized in these settings.

While the present invention is usable with respect to syringes, needles, needleless devices, or any other medical device configured to withdraw liquids from a sterile reservoir, the description herein will refer to syringes, however, such reference to syringes should be construed to include reference to any medical device configured to withdraw liquids from a sterile reservoir.

Accordingly, a system has been designed to overcome the foregoing problems of contamination. As such, the system is configured so that only one access event occurs for a sterile reservoir with a sterile syringe attached to a sterile syringe adapter. This adapter is configured to be received onto the syringe in a manner such that it must be removed before a needle or needleless system can be placed on the end of the syringe and the medication is injected into the patient. Additionally, the adapter was configured so that is can only be placed on a syringe one time. As such, once the adapter is removed from a syringe, it cannot be placed back on the syringe. Also, the system can include a back-up safety feature that is configured to prevent the adapter from allowing liquid to flow therethrough once it has been used one time. This prevents liquid from flowing from a sterile reservoir through the device once the device has already accessed a reservoir and had fluid flow therethrough.

When a syringe is placed to receive liquid from a reservoir, negative pressure or a "sucking" effect allows for the liquid to flow through the syringe. Accordingly, the adapter can include an access valve that only operates one way. After removal and use of the syringe, the access valve remains closed and does not allow for fluid to pass through the same adapter connection. The adapter and access valve is described in more detail below. At steady state and with positive pressure from the syringe, the access valve remains closed, not allowing any fluid to flow into or out of the reservoir, thus preventing accidental contamination of the reservoir.

The adapter as described herein can be removably couplable to a syringe. Also, the adapter can be removably couplable to a solution reservoir. Additionally, the adapter can be integrated to either the syringe or solution reservoir.

Development of a vacuum within a rigid solution reservoir, such as a glass bottle, occurs during liquid extraction. Once liquid (i.e. medication) is removed from a reservoir, a negative internal pressure results. This is not a problem with IV bags as the bag simply collapses under atmospheric pressure, normalizing pressures across the PVC membrane. In a rigid medication reservoir, such as a glass bottle, this problem is presently overcome by injecting air via a delivery assist device into the bottle through a valve prior to drug removal with a syringe. This issue of negative pressure can be addressed by placement of a millipore filter within a one-way valve and incorporating the filter and one-way valve into a delivery assist device such that air can enter into the rigid reservoir as fluid is extracted, thus preventing a vacuum effect. This one-way air valve and filter combination can be incorporated with delivery assist devices used only on rigid reservoirs, like a glass bottle.

The present invention relates to a safety-engineered, one-time use, syringe adaptor-connector system that restricts access to medical vials and intravenous bags (common reservoirs). Within the mechanism a delivery control valve (connector) is placed on the common reservoir, serving to limit the syringe type that can be used to access the liquid content within the reservoir. The syringe includes an adaptor, which is designed to limit access to a common reservoir to one-time use only. The system impedes the ability to access a common reservoir with a contaminated syringe.

The adoption of this safety-promoting device into medical practices provides an added measure of protection and safety that is not limited by human error, misunderstanding of safe syringe practice, or lack of education. This "lock and key" method is the most effective way in which to prevent the spread of infection through contaminated syringes.

In one embodiment, the present invention include a two-part system that has: 1) a syringe adapter that is attached to the functional tip of a syringe, where this component is attached at the time the syringe is manufactured or can be an independent safety device that can be coupled to the syringe prior to use; 2) a delivery assist device which is incorporated into the medication reservoir (e.g. IV bag, glass vial, etc.). The syringe adapter can be integrated with a syringe, or it can be removably couplable to the syringe. Once removed it cannot be reused. The adapter can be prepackaged to be coupled to a syringe, and then the adapter can be removed from the syringe so that the syringe can receive a needle or the like. The delivery assist device can be integrated with a liquid reservoir (e.g., container), or it can be removably coupled to the liquid reservoir.

The components of the system are configured such that in order to access liquid from a bottle or bag that has the delivery assist device in place, a syringe adaptor must be utilized. This system would not allow an individual with a standard syringe & needle to access the medication. The syringe adapter can be placed on the syringe at the time of manufacturing and subsequently sterilized. With this adapter, the liquid can be removed from its reservoir when the reservoir has the delivery assist device. Once the liquid is in the syringe, the syringe adaptor will not allow access of an IV or other tubes contaminated with body fluids. The syringe adapter must be removed from the syringe before a needle can be placed on the syringe such that patient IV access can occur. Once the adapter is removed, the design will not allow it to be placed back on a syringe. Before additional liquid can be accessed from the reservoir again, a new sterile syringe and syringe adapter must be used. This two part "lock and key" design (e.g., 1 component built into the liquid reservoir and 1 component attached to the syringe) prevents access of a liquid from a common reservoir via a contaminated syringe. A functional "lock" (delivery assist device) and a "key" (syringe adapter) that does not allow someone to access that medication reservoir with a non-sterile syringe can be important to stop the reservoir from being contaminated. Once used, the syringe adapter is rendered useless with the delivery assist device.

In one embodiment, as an added safety feature the delivery assist device, located on the liquid reservoir, can be designed such that any positive pressure from a syringe will not allow flow of contaminated material back into the common reservoir. An example can include a one-way valve in the delivery assist device, but other safety features can be used. This design can help prevent potential "work-arounds", i.e. trying to find a way to use a standard syringe to access the liquid through this delivery device.

In one embodiment, the delivery assist device and/or syringe adapter can employ electronics or a mechanical system that only allows the delivery assist device to open only for a new and sterile syringe adapter. For example, the electronics or a mechanical system can be configured to only open a valve or otherwise allow access to the reservoir with a sterile syringe adapter (e.g., unused).

For example, there may be a small chip on the delivery assist device that recognizes if a given adapter has already been allowed access to this delivery assist device or to another delivery assist device. If this is the case, the electronics or mechanical system won't allow flow of the fluid from the reservoir through the deliver assist device (or valve therein). Alternatively, the electronics or mechanical system do not allow full coupling of the adapter to the delivery assist device, thus not allowing one to create the negative pressure needed to extract the fluid from the reservoir. As an example, in the case of the 2-way valve mechanism (e.g., FIG. 16), the electronics would not allow the valve to open.

Figure 1B:
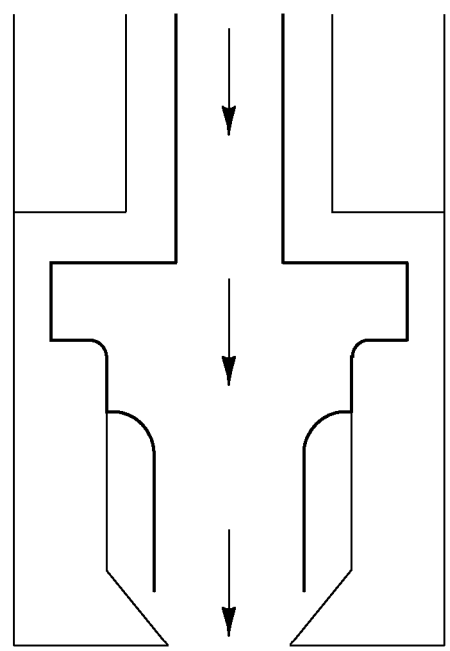
Figure 2:
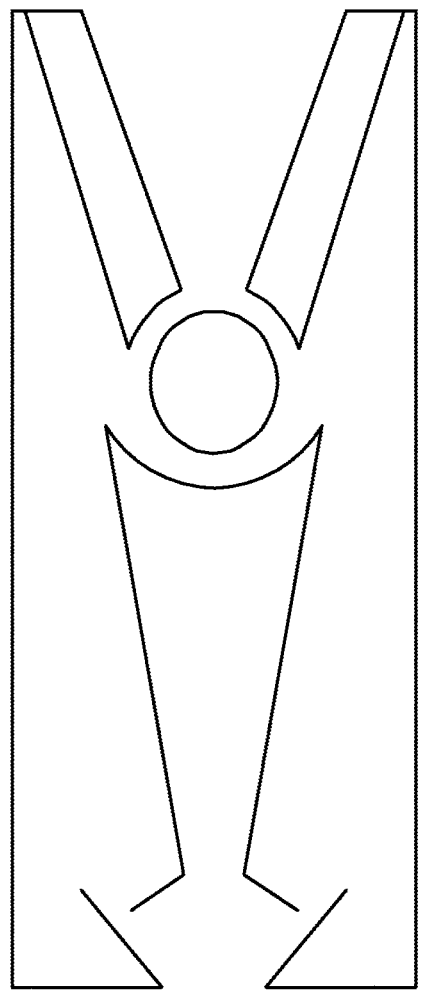
Figure 3A:
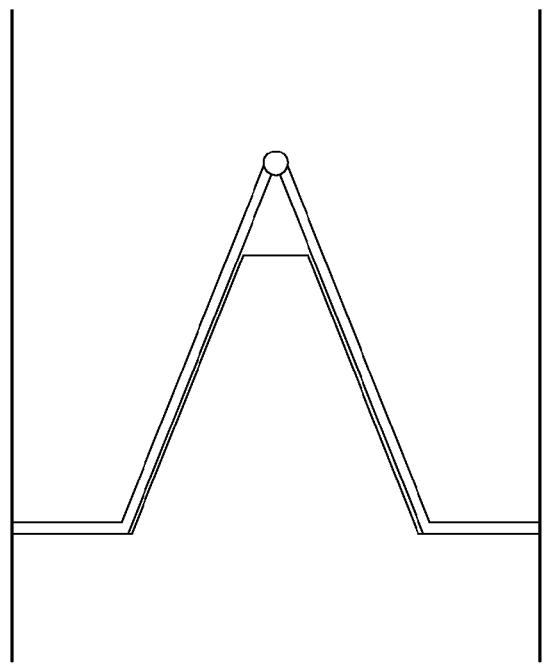
Figure 3B:
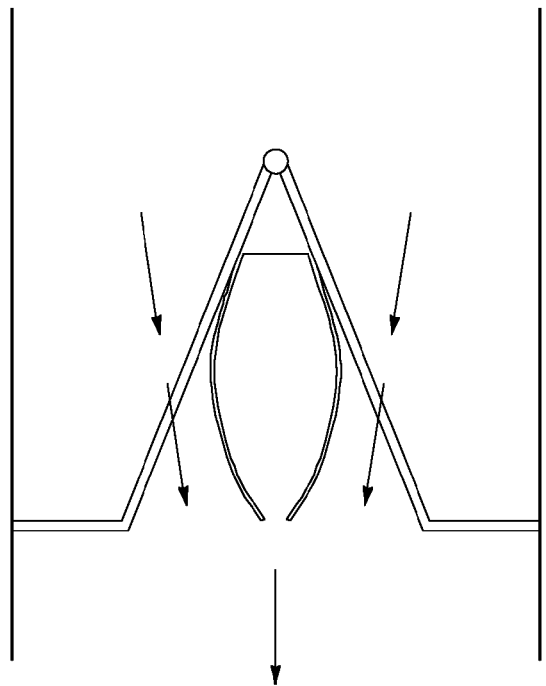

The connector includes a one-way valve, to allow for uni-directional flow of the fluid, and an internal pressure relief device, used to relieve a negative pressure within the medication vial. This allows the fluid to transfer from the vial to the syringe. Below are the possible choices for one-way valves and pressure relief devices:

FIG. 1A describes a duckbill valve in a closed position and FIG. 1B shows the duckbill valve in an open position with the arrows indicating the one way direction of fluid flow. FIG. 2 shows a ball check valve in an open position. FIGS. 3A and 3B show a diaphragm vale in the closed and open positions respectively. The arrows in FIG. 3B indicate one way flow of fluid. Other valve types that can be used include tilting disc valve, swing check valve, lift check valve, or plug check valve.

Figure 4:
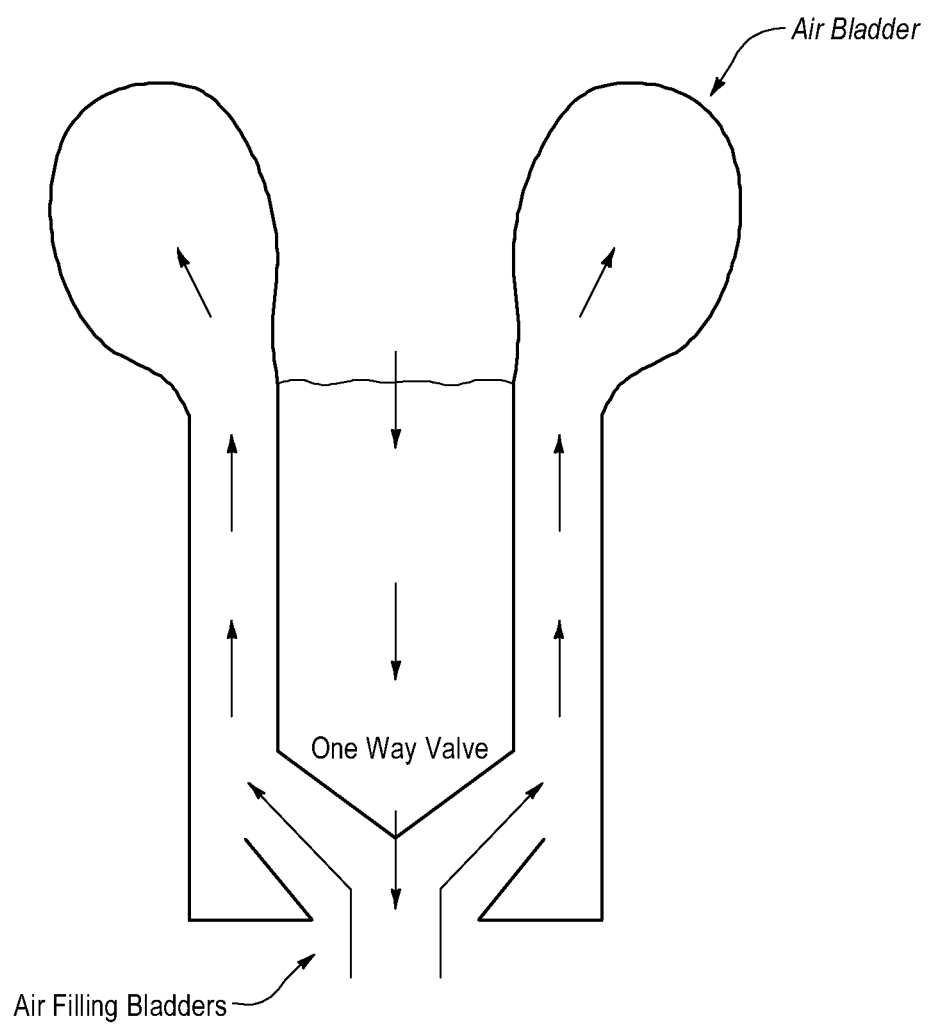
Figure 5A:
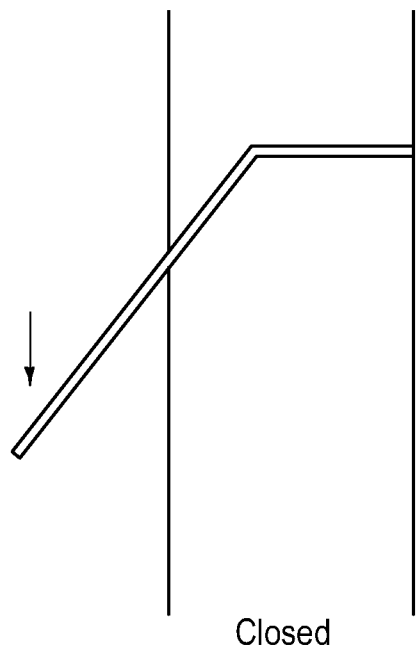
Figure 5B:
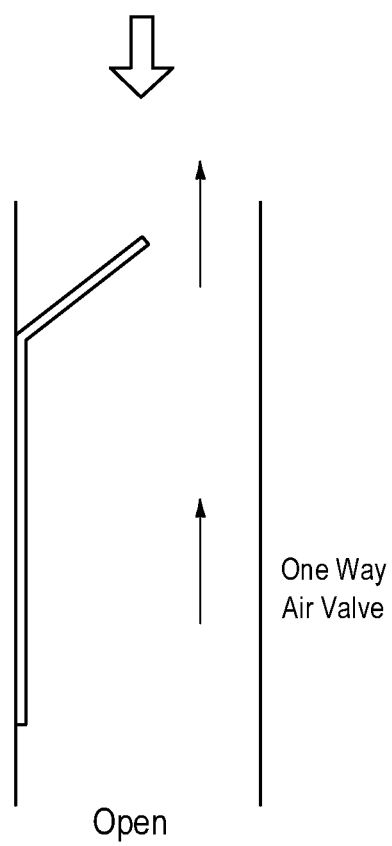
Figure 6A:
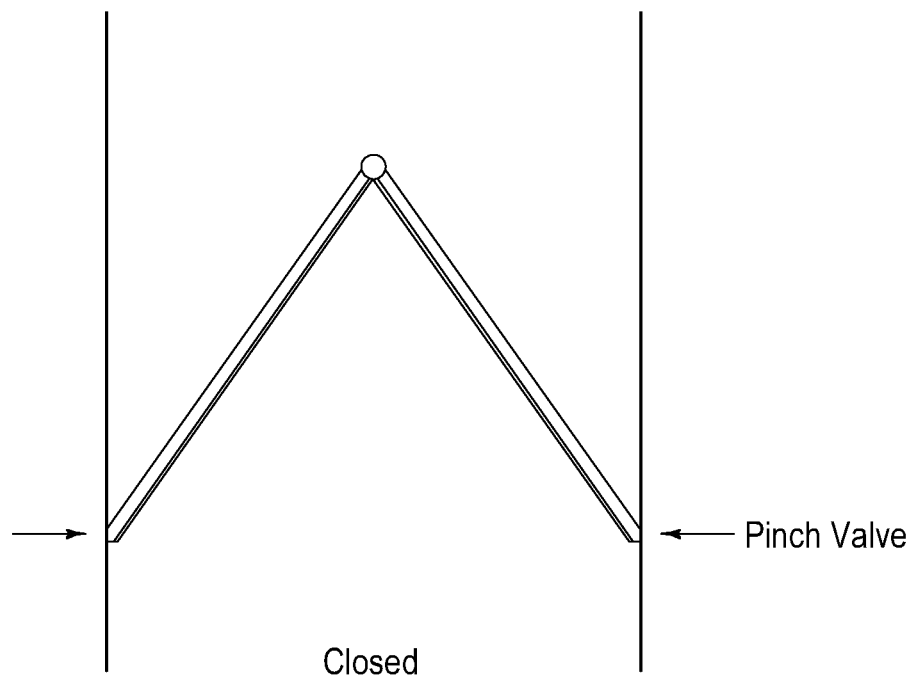
Figure 6B:
Figure 6B:
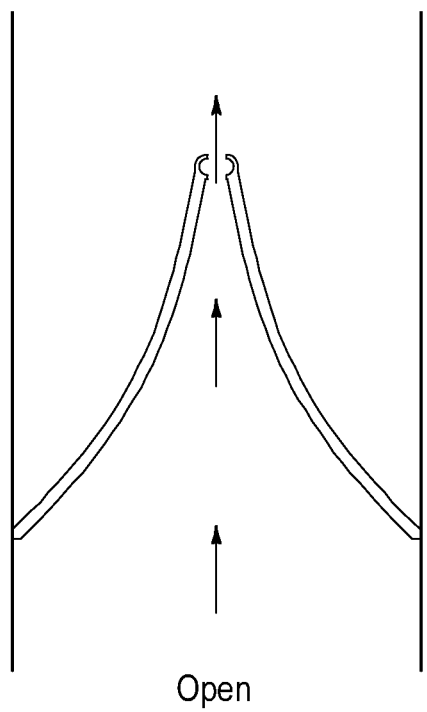
Figure 7:
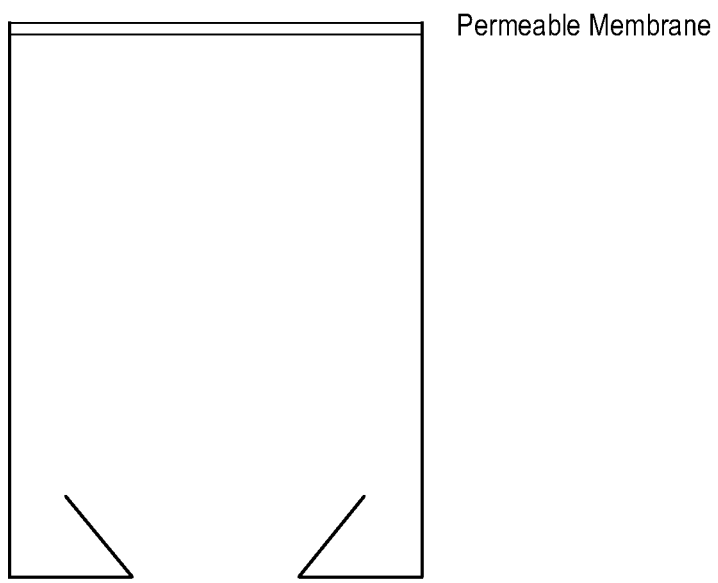

FIG. 4 shows a pressure relieve valve with an rubber membrane for pressure release. FIGS. 5A and 5B show one way valves for pressure release. FIGS. 6A and 6B show one way pressure valves that can be activated by pinching. FIG. 6A shows the pinch valve in the closed position and FIG. 6B shows the pinch valve in the open position with the vertical arrows indicating the direction of air flow. FIG. 7 shows an adaptor with a one way permeable membrane.

Figure 10:
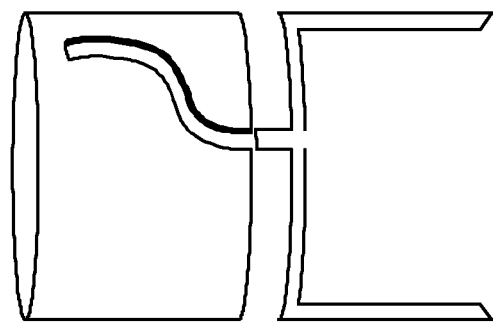
Figure 9:
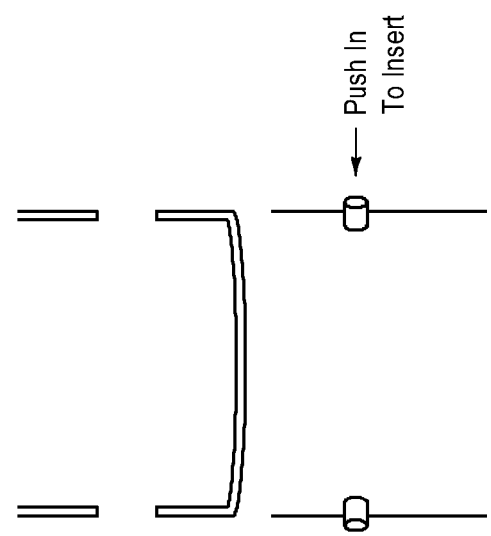
Figure 8:
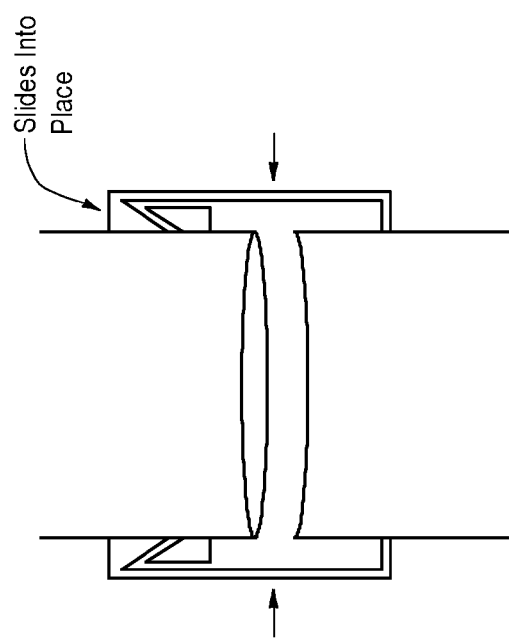
Figure 11:
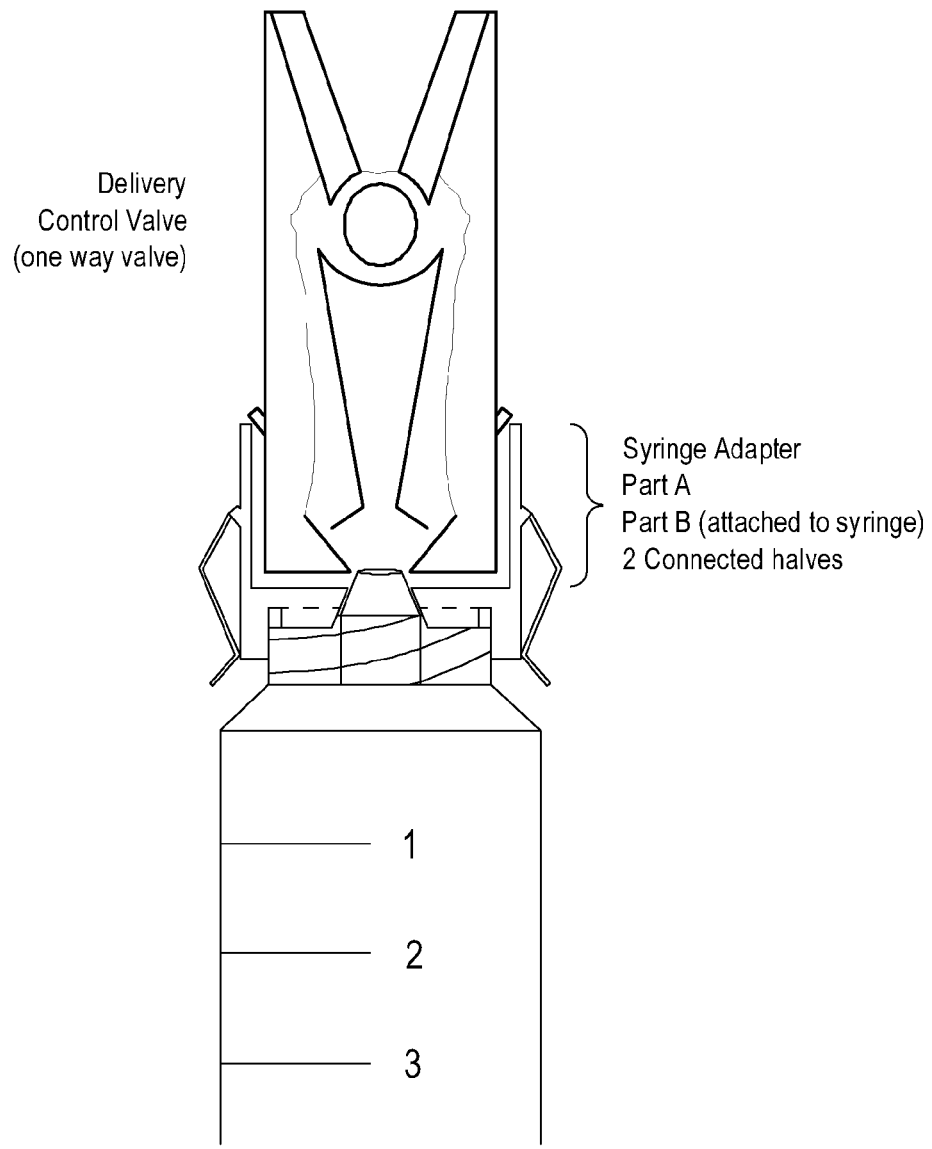

FIGS. 8 to 10 show attachment mechanisms for connecting the adaptor to the reservoir and preventing fluid from being withdrawn using a needle. When using the connectors shown herein a needle will not be used to transfer fluid from the common reservoir to the syringe. Rather, the connector prevents a luer lock needle from being placed on the syringe until the adaptor has been removed from the syringe. FIG. 8 shows the adapter mechanism for connecting to a syringe using a sawtooth mechanism in which the sides can be pushed in to allow attachment and release of the adaptor from a connector. FIG. 9 illustrates a push release mechanism in which pushing the tabs on the adaptor in allows the adaptor to be inserted into the connector. Tabs should "pop" into place in the holes on the connector. FIG. 10 shows a groove mechanism that allows the adaptor to connect to a connector by turning the adaptor clockwise to lock it in place in the groove. FIG. 11 shows a system that can be attached to a reservoir for drug delivery. The upper portion is a one way fluid valve connected to a syringe adapter that includes two separable connected halves attached to and separating the syringe from the drug delivery control valve. Part A includes a squeezable clamp similar to the mechanism shown in FIG. 8, which "pops" part B off of the syringe when compressed.

To limit the syringe to one-time use only, the adaptor itself can be locked out or otherwise become inoperable for connecting or otherwise being usable as an adapter to transfer fluid from a liquid reservoir. This can occur via several different mechanisms. In one embodiment, the adaptor can be deformed or mechanically altered when separated from the reservoir, or alternatively can be physically broken apart.

The adaptor can have a unibody design, which can include engineered perforations; enabling the adaptor to either separate into individual parts or plastically deform upon removal from the connector. Once the adaptor portion of the syringe has been dismembered it cannot be reassembled to build a functioning adaptor again, preventing re-use of the syringe.

Figure 12:
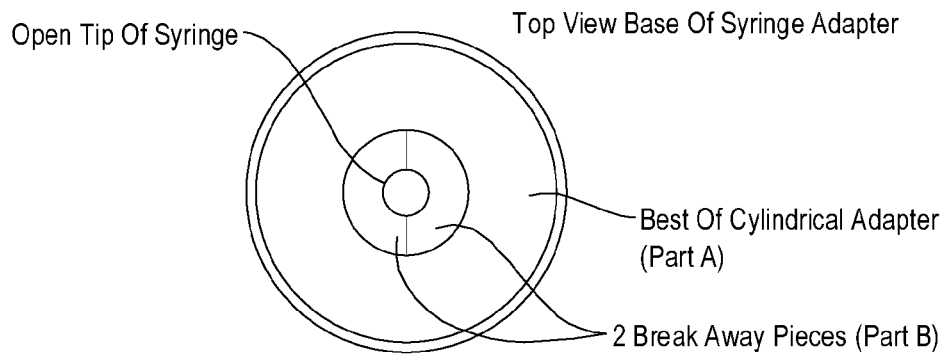
Figure 13:
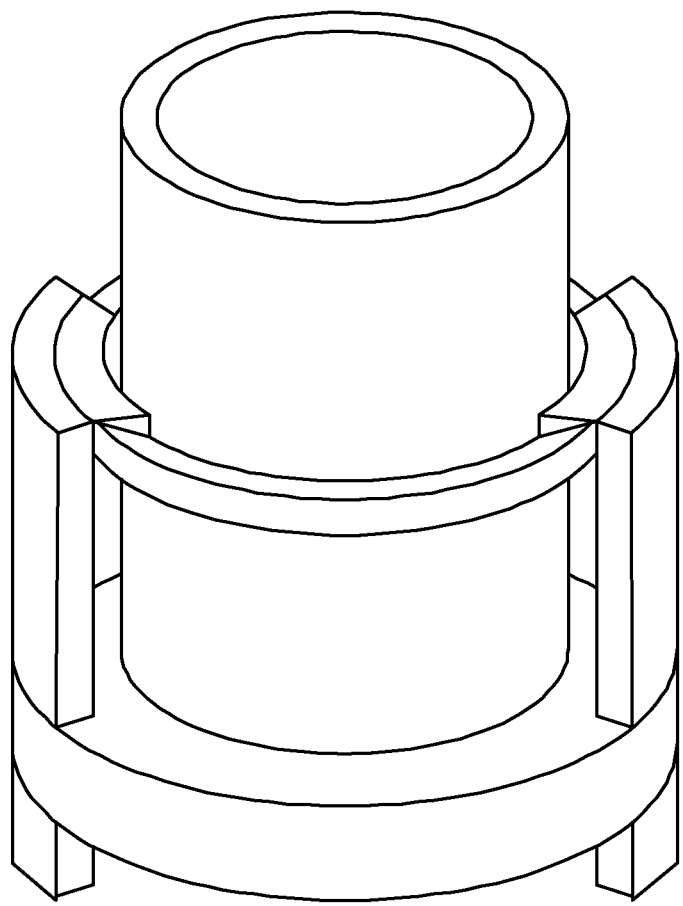

FIG. 12 illustrates an adapter that has a first part and a second part that break apart after being disconnected from the first time use. FIG. 13 is a drawing of the adapter (located on the syringe) connected with the connector. FIG. 13 illustrates an adaptor with a plastic "pull tab", similar to that of a milk carton. In order to physically place the luer lock needle on the syringe the, "pull tab" must first be removed from the adaptor. Once this has been done, it will be physically impossible to reattach the adaptor to the syringe, limiting the syringe to one-time use only. At the same time, if the "pull tab" is removed from the adaptor prior to connection with the connector, one will not be able to obtain fluid from the common reservoir, because a proper connection will no longer be possible between the adaptor and connector.

Figure 14:
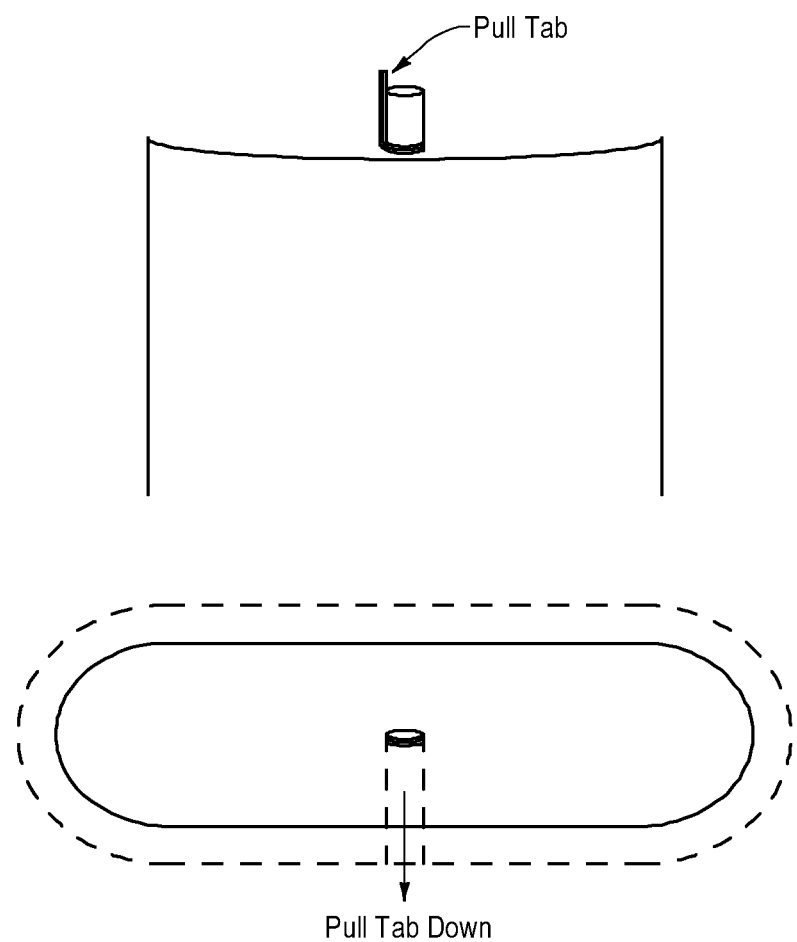

FIG. 14 illustrates a pull tab mechanism. To render the adapter inoperable, the user pulls the tab downward from the center and continues pulling around the entire circumference of adaptor until detachment occurs from the syringe.

While many of the drawings represent as a cylindrical shape, the shape of the components is not limited to a cylinder, and could be produced in many forms including a square, rectangle, oval, star, hexagon, or pentagon etc.

Examples of suitable materials that can be used to make the syringe adapter include, but are not limited to, silicone elastomers, which can be used for flexible components such as membranes and flexible body. Stainless steel can be used in fluid pathway components. Polyester can be used in external housing of adaptor or connector. Polyethylene can be used for fluid pathways within the device. Polycarbonate can be used in external housing where clarity, strength, and tight connections are important. Polypropylene can be used in internal or external housing of adaptor and connector.
Alternate Design Specifications:

In the first design, one way flow is required. This provides a secondary safety mechanism, preventing backflow in addition to preventing syringe reuse. However, one could use only one of the safety mechanisms in the design. Therefore an alternate design is one that prevents syringe reuse but allows for flow in both directions. Such a design would not require a pressure equalization method.

In this embodiment, the system can allow flow in both directions (into and out of the syringe) but will be open only during connection of the connector to the adaptor. The system cannot be open with a needle, instead the system will contain an intrinsic key in which to open the system. In this embodiment, the system should be made inoperable upon disconnect to prevent reuse. The system should not function when a needle is used to tamper with the system.

Another method of using a "lock and key" mechanism would be to place a duckbill (or other) valve in the connector which is manually open the valve upon insertion of the adaptor, allowing flow in either direction. This would occur with a "key" located on the adaptor that would manually push the gates of the valve open. The key would be of a shape other than a needle in order to prevent tampering of the device. This will eliminate the need for a pressure relief device, allowing one to physically push air in and pull fluid out once the syringe adaptor has been connected to the connector.

Figure 15:
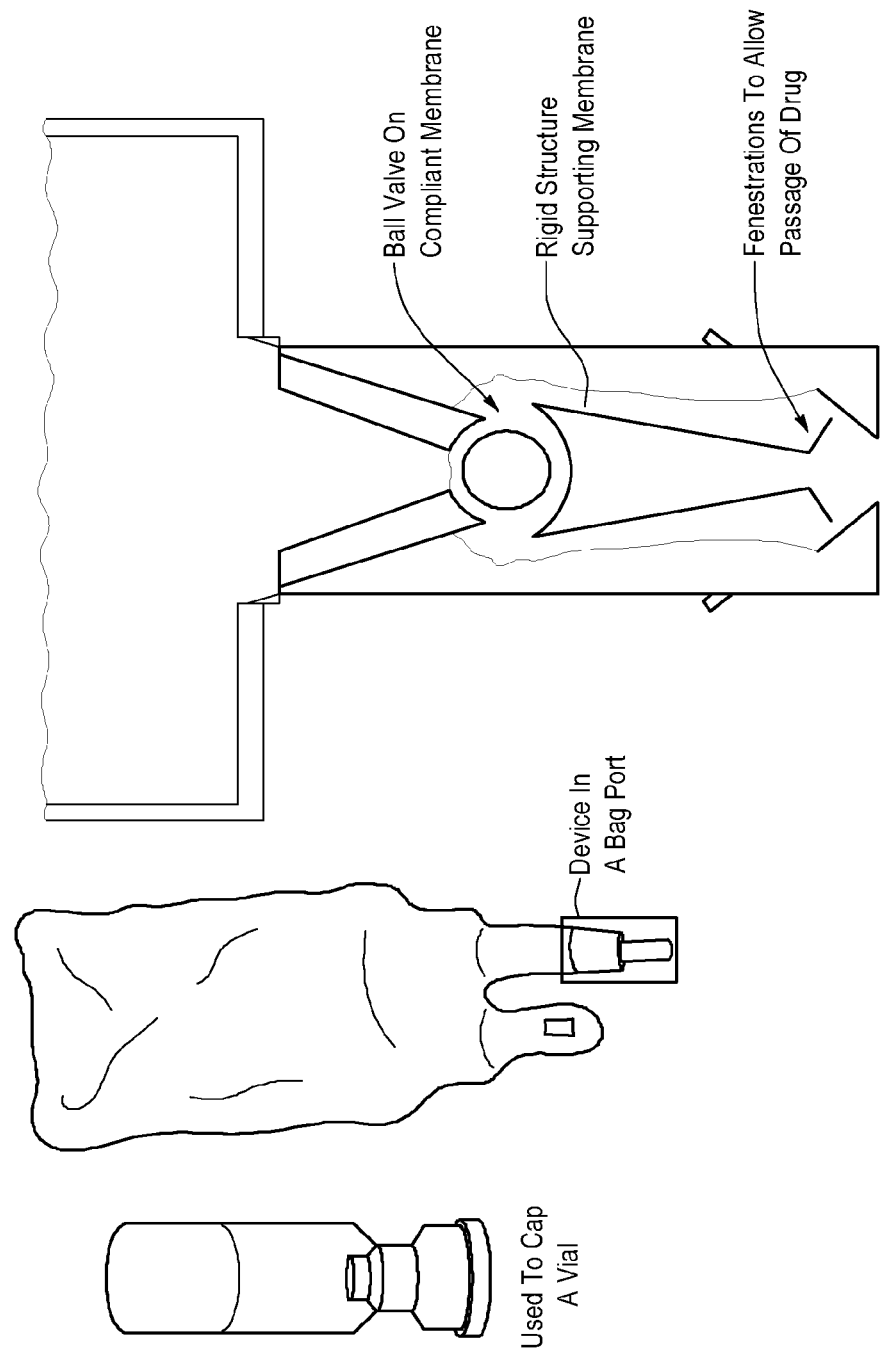
Figure 16C:
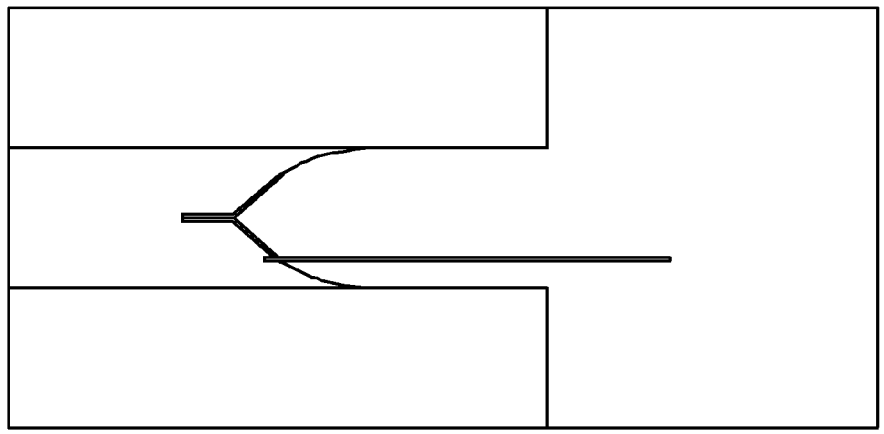
Figure 16B:
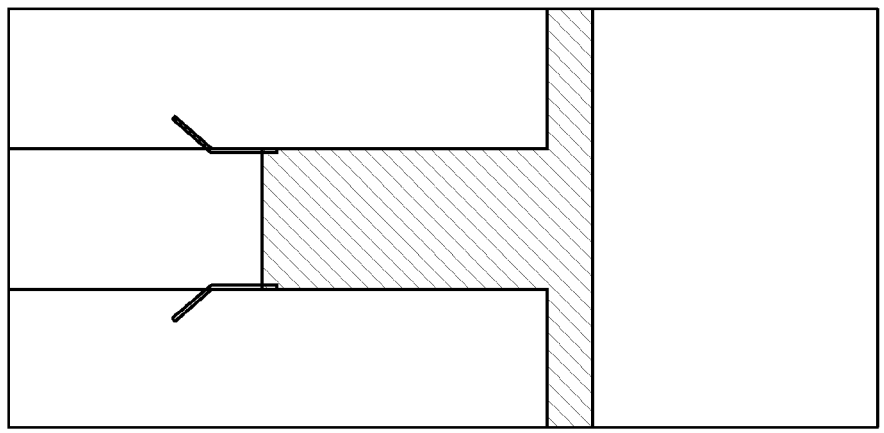
Figure 16A:
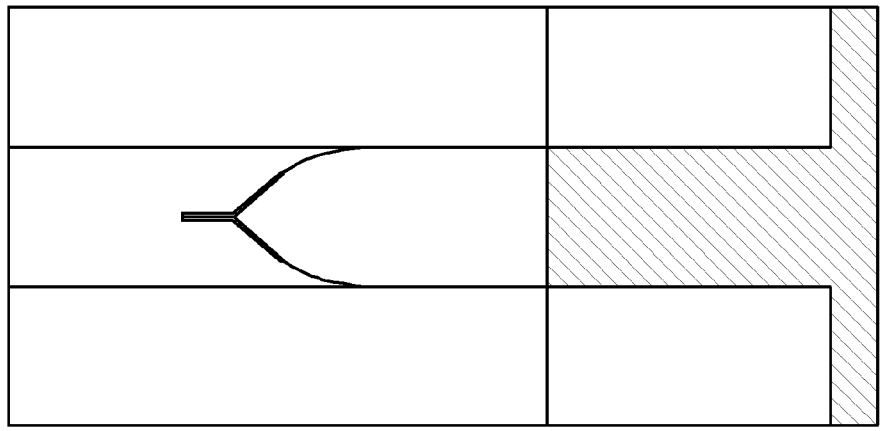

FIG. 15 illustrates a system according to the invention in which the adaptor is connected to a reservoir. FIG. 16A-16C illustrate an example of a two-way valve mechanism. In 16A, the two way valve is closed. In FIG. 16B the adapter is open. In FIG. 16C the valve is open, but a needle is physically blocked from being inserted.

Figure 17:
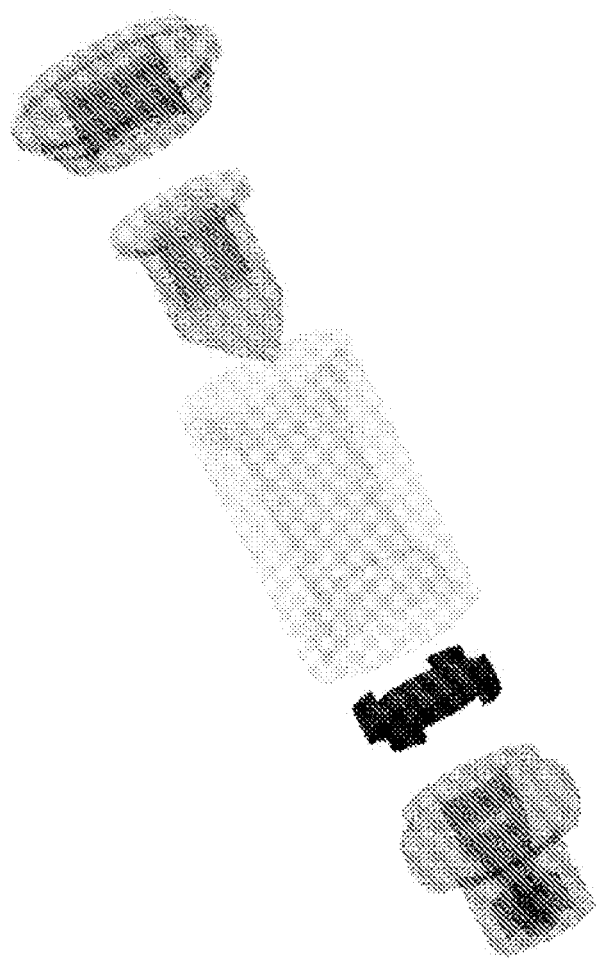

FIG. 17 shows an exploded view of a valve assembly including (from top to bottom) a valve cap, a duck valve (one way valve), assembly body, needle stop, and syringe mate. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein by specific reference in their entirety.

The invention claimed is:

1. A safety system for inhibiting contamination of a liquid reservoir, the system comprising:
a syringe adapter configured for a one time use, the syringe adapter comprising a pull tab,
wherein the syringe adapter is configured to disassemble, deform or split when removed from a syringe upon manipulation of the pull tab such that the syringe adapter is rendered unusable and unable to be reassembled, thus preventing re-use of the syringe with the syringe adapter.

2. The safety system of claim 1, wherein the syringe adapter is coupled to a syringe or integrated with the syringe or removably coupled to the syringe.

3. The safety system of claim 1, further comprising a common reservoir.

4. The safety system of claim 3, further comprising a connector connected to the common reservoir.

5. The safety system of claim 4, wherein the syringe adapter is connected to the connector.

6. The safety system of claim 2, wherein the syringe is a needleless syringe.

7. The safety system of claim 2, wherein the syringe is a syringe with a needle.

8. The safety system of claim 2, further comprising a common reservoir.

9. The safety system of claim 8, further comprising a connector connected to the common reservoir.

10. The safety system of claim 9, wherein the syringe adapter is connected to the connector.

11. The safety system of claim 8, wherein the syringe is a needleless syringe.

12. The safety system of claim 8, wherein the syringe is a syringe with a needle.

13. A safety system for inhibiting contamination of a liquid reservoir, the system comprising:
a common reservoir;
a connector connected to the common reservoir;
a syringe;
a syringe adapter configured for a one time use and connected to the common reservoir by the connector, the syringe adapter comprising a pull tab, the syringe adapter is coupled to the syringe wherein the syringe adapter is configured to disassemble, deform or split when removed from the syringe upon manipulation of the pull tab such that the syringe adapter is rendered unusable and unable to be reassembled, thus preventing re-use of the syringe with the syringe adapter.

14. The safety system of claim 13, wherein the syringe is a needleless syringe.

15. The safety system of claim 13, wherein the syringe is a syringe with a needle.

16. A method of withdrawing liquid from a liquid reservoir, the method comprising:
  providing the safety system of claim 13;
  coupling the syringe adaptor to the connector;
  withdrawing liquid from the common reservoir through the syringe adaptor;
  decoupling the syringe adaptor from the common reservoir; and
  removing the pull tab from the syringe adaptor such that the syringe adapter is rendered unusable.

\* \* \* \* \*